United States Patent
Thurner

(10) Patent No.: US 6,567,999 B1
(45) Date of Patent: May 27, 2003

(54) SHOWER STALL UNIT WITH INTEGRAL TANNING LIGHTS

(76) Inventor: Keith L. Thurner, 21 Sawmill Rd., Finleyville, PA (US) 15332

( * ) Notice: Subject to any disclaimer, the term of this patent is extended or adjusted under 35 U.S.C. 154(b) by 0 days.

(21) Appl. No.: 10/046,877

(22) Filed: Jan. 14, 2002

(51) Int. Cl.[7] .............................. A47K 3/22; A47K 3/28
(52) U.S. Cl. ................ 4/597; 4/612; 4/614; 4/610; 250/494.1; 607/80
(58) Field of Search ........................ 4/597, 598, 612, 4/614; 250/494.1; 607/80, 82, 94

(56) References Cited

U.S. PATENT DOCUMENTS

| | | | |
|---|---|---|---|
| 3,007,178 A | * 11/1961 | Altman et al. ................ | 4/525 |
| 4,095,113 A | 6/1978 | Wolff | |
| 4,130,120 A | * 12/1978 | Kohler, Jr. .................... | 607/80 |
| 4,287,554 A | 9/1981 | Wolff | |
| 4,424,598 A | * 1/1984 | Cima .............................. | 4/612 |
| 4,623,796 A | 11/1986 | Kratz | |
| 4,703,184 A | 10/1987 | Wolff | |
| 4,829,608 A | * 5/1989 | Stevens et al. ................ | 4/597 |
| 6,139,568 A | 10/2000 | Doty | |
| 6,208,069 B1 | 3/2001 | Justel et al. | |
| 6,226,454 B1 | 5/2001 | Couture | |
| 6,265,835 B1 | 7/2001 | Parra | |

FOREIGN PATENT DOCUMENTS

DE                3500367 A1 * 7/1986 ..................... 4/597

* cited by examiner

Primary Examiner—Steven O. Douglas
Assistant Examiner—Tuan Nguyen
(74) Attorney, Agent, or Firm—John D. Gugliotta; Olen L. York, III

(57) ABSTRACT

A shower stall with integral tanning lights is provided. The shower stall has two tanning light units mounted on two adjacent walls of the shower, each containing tanning bulbs behind tempered glass panels. The panels are securely fastened with waterproof gasketing, and are flush mounted into the bath or shower unit stall wall. A waterproof control panel provides for control of the tanning lights and utilizes a timer to prevent over exposure. Other components necessary for proper operation, such as ballasts, reflectors, wiring and the like are mounted behind the shower or bath stall wall, in the wall stud cavity.

7 Claims, 3 Drawing Sheets

SHOWER STALL UNIT WITH INTEGRAL TANNING LIGHTS

RELATED APPLICATIONS

The present invention was first described in Disclosure Document Registration 498,436 filed on Aug. 16, 2001 under 35 U.S.C. §122 and 37 C.F.R. §1.14. There are no previously filed, nor currently any co-pending applications, anywhere in the world.

BACKGROUND OF THE INVENTION

1. Field of the Invention

The present invention relates generally to shower stalls and, more particularly, to a shower stall with integral tanning lights on the interior thereof.

2. Description of the Related Art

The perfect, golden tan is a pursuit of many. Much time, effort and money are spent outdoors, in tanning booths, and on special lotions and oils to generate and maintain the ideal tan. However, many people simply do not have the time to spend in such pursuits, but desire a great tan nonetheless. Such time is necessary whether lying outdoors, driving to a tanning salon, or rubbing in lotions. Even the lucky user who has their own personal tanning bed or booth in their own home, must spend time in such;devices while doing nothing else.

A search of the prior art did not disclose any patents that read directly on the claims of the instant invention; however, the following references were considered related.

U.S. Pat. No. 4,095,113, issued in the name of Friedrich Wolff, describes an apparatus for treatment of humans with ultraviolet rays U.S. Pat. No. 4,287,554, issued in the name of Friedrich Wolff, describes an apparatus for producing ultraviolet radiation for tanning or therapeutic reasons U.S. Pat. No. 4,623,796, issued in the name of Walter Kratz, describes a tanning apparatus.

U.S. Pat. No. 4,703,184, issued in the name of Friedrich Wolff, describes a full-sized skin tanning apparatus.

U.S. Pat. No. 6,139,568, issued in the name of John S. Doty, describes a tanning bed apparatus.

U.S. Pat. No. 6,208,069, issued in the name of Thomas Justel, et al, describes a low pressure mercury discharge lamp for tanning.

U.S. Pat. No. 6,226,454, issued in the name of Pierre Couture, describes an apparatus and method for heating at a distance by light radiance.

U.S. Pat. No. 6,265,835, issued in the name of Jorge M. Parra, describes ultraviolet treatment and purification system.

Consequently, a there exists a need for a means by which a golden tan may be obtained in a concurrent manner with other everyday activities in a manner which is quick, easy and effective.

SUMMARY OF THE INVENTION

It is therefore an object of the present invention to provide an improved means of obtaining a tan.

It is a feature of the present invention to allow a means of obtaining a tan while taking a shower.

It is a feature of the present invention to include the features of a tanning booth and a shower in one integral unit.

Briefly described according to one embodiment of the present invention, a shower stall with integral tanning lights is provided. The shower stall has two tanning light units mounted on two adjacent walls of the shower, each containing tanning bulbs behind tempered glass panels. The panels are securely fastened with waterproof gasketing, and are flush mounted into the bath or shower unit stall wall. A waterproof control panel provides for control of the tanning lights and utilizes a timer to prevent over exposure. Other components necessary for proper operation, such as ballasts, reflectors, wiring and the like are mounted behind the shower or bath stall wall, in the wall stud cavity. The invention is intended for use in new construction or during major bathroom remodeling.

The use of the present invention allows a user to acquire a deep, golden tan while taking a shower in a manner which is quick, easy and effective.

BRIEF DESCRIPTION OF THE DRAWINGS

The advantages and features of the present invention will become better understood with reference to the following more detailed description and claims taken in conjunction with,the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures.

1. Detailed Description of the Figures

Figure 1:
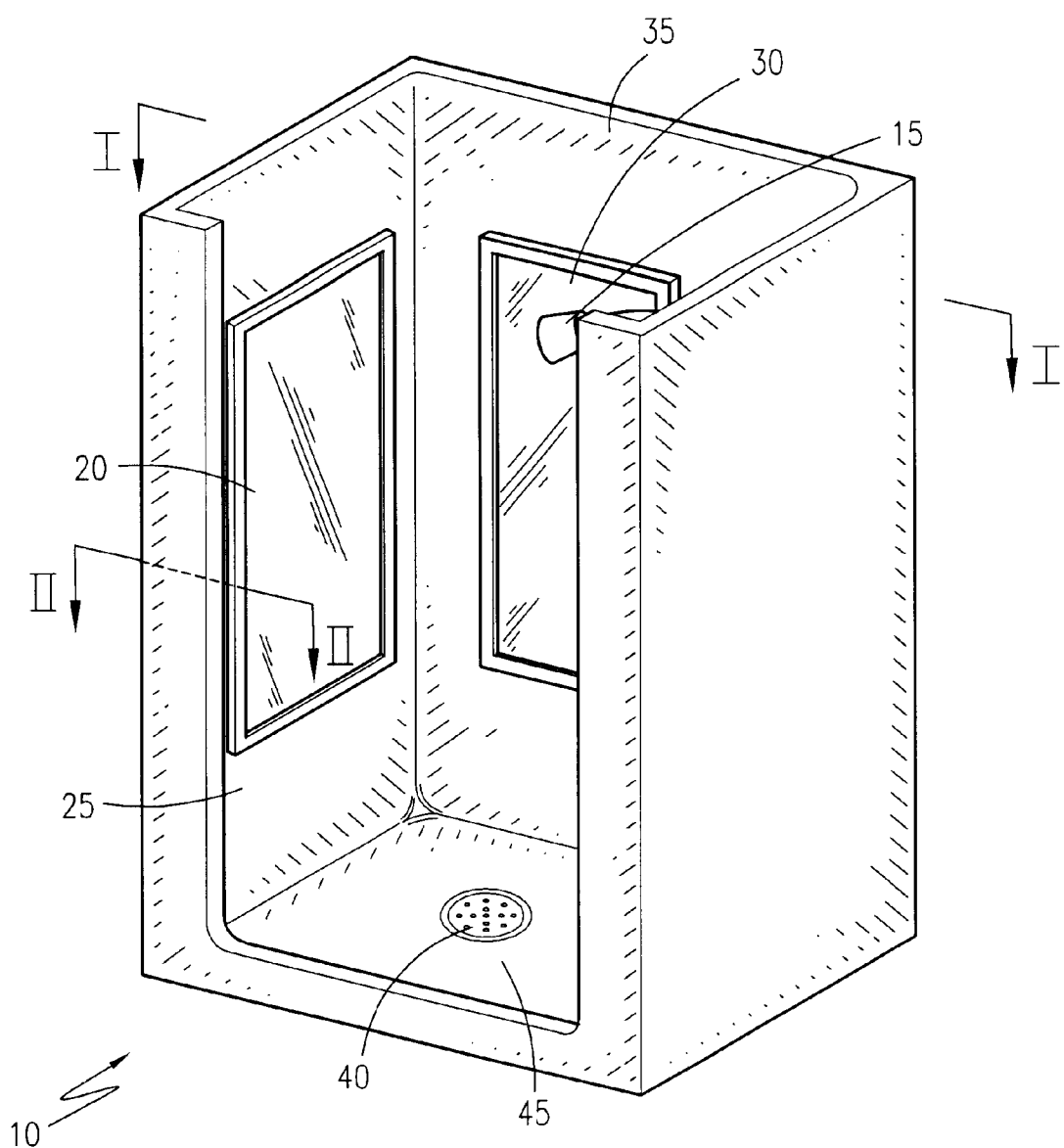
FIG. 1 is an isometric view of a shower stall with integral tanning lights 10 according to the preferred embodiment of the present invention.

Referring now to FIG. 1, a shower stall with integral tanning lights 10 is shown, according to the preferred present invention. The shower stall with integral tanning lights 10 is of a standard size and configuration as a conventional shower stall and is envisioned to have dimensions of three feet deep, three feet wide and six to seven feet tall. A standard door section is also provided but is omitted from this FIG. for purposes of clarity. A shower head 15 is visible on the right hand side of the shower stall with integral tanning lights 10. The shower head 15 could also be provided on the left hand side of the shower stall with integral tanning. lights 10 depending on installation requirements, and for further discussion purposes it shall be assumed that the shower stall with integral tanning lights 10 is capable of being provided in both right and left hand versions. A side mounted tanning light 20 is provided on a shower side wall 25 and a rear mounted tanning light 30 is provided on a shower rear wall 35. The side mounted tanning light 20 and the rear mounted tanning light 30 will be described in greater detail herein below. A drain 40 is provided on the floor 45 of the shower stall with integral tanning lights 10 to allow it to function as a conventional shower, for those times that the functionality of the side mounted tanning light 20 and side mounted tanning light 20 is not desired or necessary. It is also envisioned that for those shower stalls that utilize a top or roof, an additional tanning light would be provided in the roof, thus allowing tanning of the user from the top thereof. The top mounted light would be installed and function in a manner identical to that of the side mounted tanning light 20 and rear mounted tanning light 30 and are omitted for purposes of clarity in this FIG. as well as following discussions, but should not be interpreted as a limiting factor of the invention. The shower side wall 25, the shower rear wall 35, the floor 45 as well as all components of the shower would be made of fiberglass, heavy plastic, or of other components commonly used in the construction of conventional shower stalls.

Figure 2:
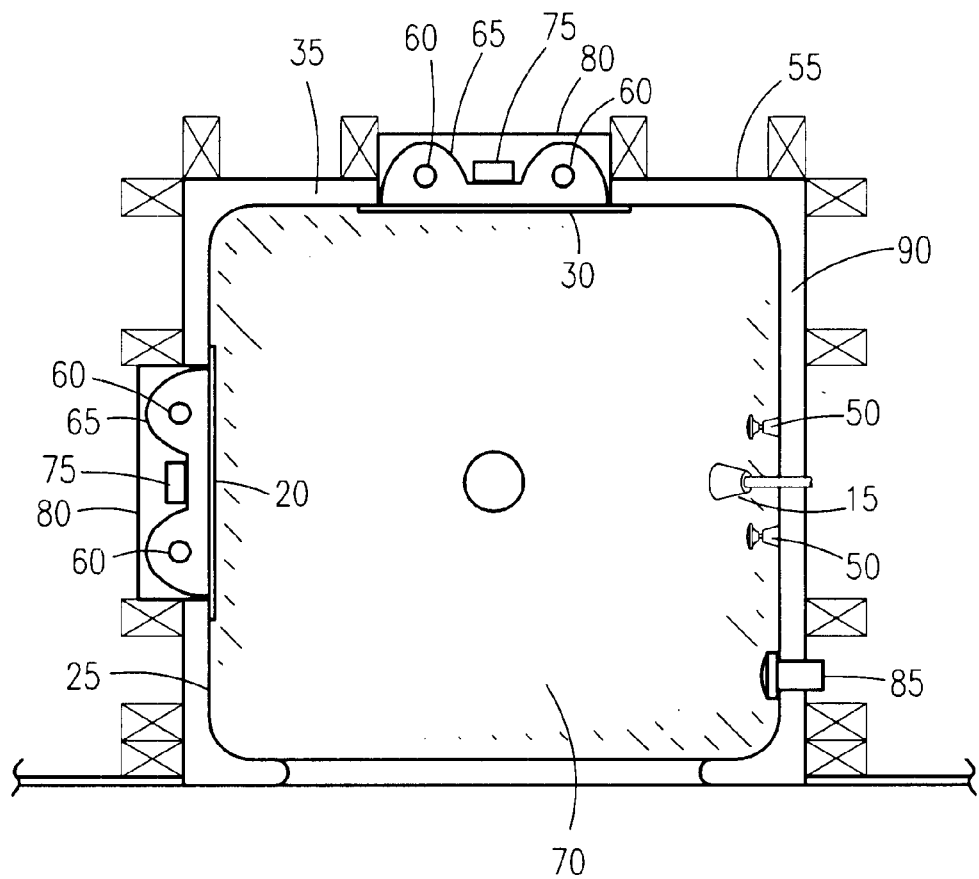
FIG. 2 is a sectional view of the shower stall with integral tanning lights 10 taken along a line I—I as seen in FIG. 1.

Referring next to FIG. 2, a sectional view of the shower stall with integral tanning lights 10 as seen along a line I—I in FIG. 1, is depicted. The shower head 15, along with a set of shower controls 50 are visible along the right side of the shower stall with integral tanning lights 10, and function in a conventional manner. The shower stall with integral tanning lights 10 is located within a series of wall studs 55 as would be found in common residential and commercial construction techniques. The spacing of the wall studs 55 is such that the side mounted tanning light 20 and rear mounted tanning light 30 would fit within the cavity formed by the wall studs 55 thereof. It is envisioned that the cavity formed could be also be made by conventional framing techniques used in the framing of windows with the use of header and sill plates. A pair of fluorescent tanning tubes 60 are located on the interior of each side mounted tanning light 20 and rear mounted tanning light 30 thereof. A parabolic reflector 65 surrounds each fluorescent tanning tubes 60 and refocuses rearward light rays from the fluorescent tanning tubes 60 to a shower stall interior 70. A ballast 75 is mounted to the rear surface of the parabolic reflector 65 along with internal wiring and any other necessary electrical components commonly found in a fluorescent light. Finally, a rear housing 80 forms a complete electrical enclosure about the side mounted tanning light 20 and the rear mounted tanning light 30. A timer and control mechanism 85 is located on a shower front wall 90 for ease of user operation. The timer and control mechanism 85 is of conventional and waterproof design that allows for variable operating times envisioned to be a maximum of fifteen minutes at one time. In this manner, dangerous user overexposure is avoided. Internal wiring from the power source to the timer and control mechanism 85 and interconnecting the timer and control mechanism 85 to the side mounted tanning light 20 and the rear mounted tanning light 30 would be routed through the wall studs 55 in a conventional manner. The 90° relationship of the side mounted tanning light 20 and the rear mounted tanning light 30 ensure complete coverage of the user located in the shower stall interior 70 with minimal user rotation.

Figure 3:
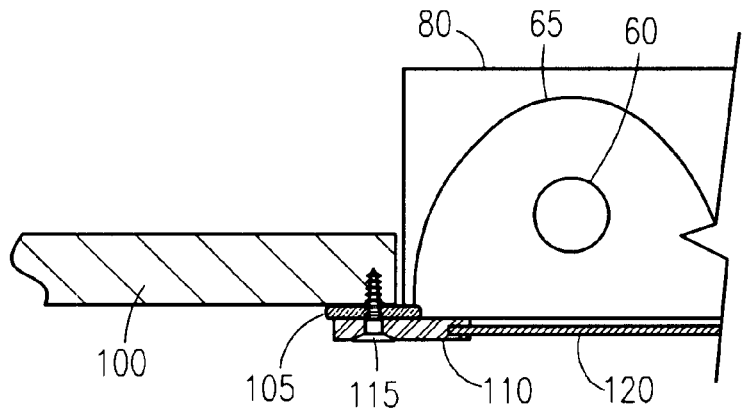
FIG. 3 is a sectional view taken along a line II—II as seen in FIG. 1.

Referring next to FIG. 3, a sectional view, as seen along a line II—II as seen in FIG. 1, is depicted. A shower wall section 100 is depicted as shown. The shower wall section 100 is typical for the shower side wall 25 or the shower rear wall 35 (as shown in FIG. 1). The shower wall section 100 is in direct physical contact with a waterproof gasket 105 which is in direct contact with a frame assembly 110. The waterproof gasket 105 is held in compression by a fastening means 115 such as a screw. The frame assembly 110 holds a piece of tempered glass 120 with the frame assembly 110 surrounding the entire perimeter of the tempered glass 120 thereof. In such a manner, a waterproof barrier is formed between the shower stall interior 70 (as shown in FIG. 2), and the interior formed by the combination of the rear housing 80 and the tempered glass 120. This allows the fluorescent tanning tubes 60, the parabolic reflector 65 and other components not shown in this view to remain dry and safely operational.

Figure 4:
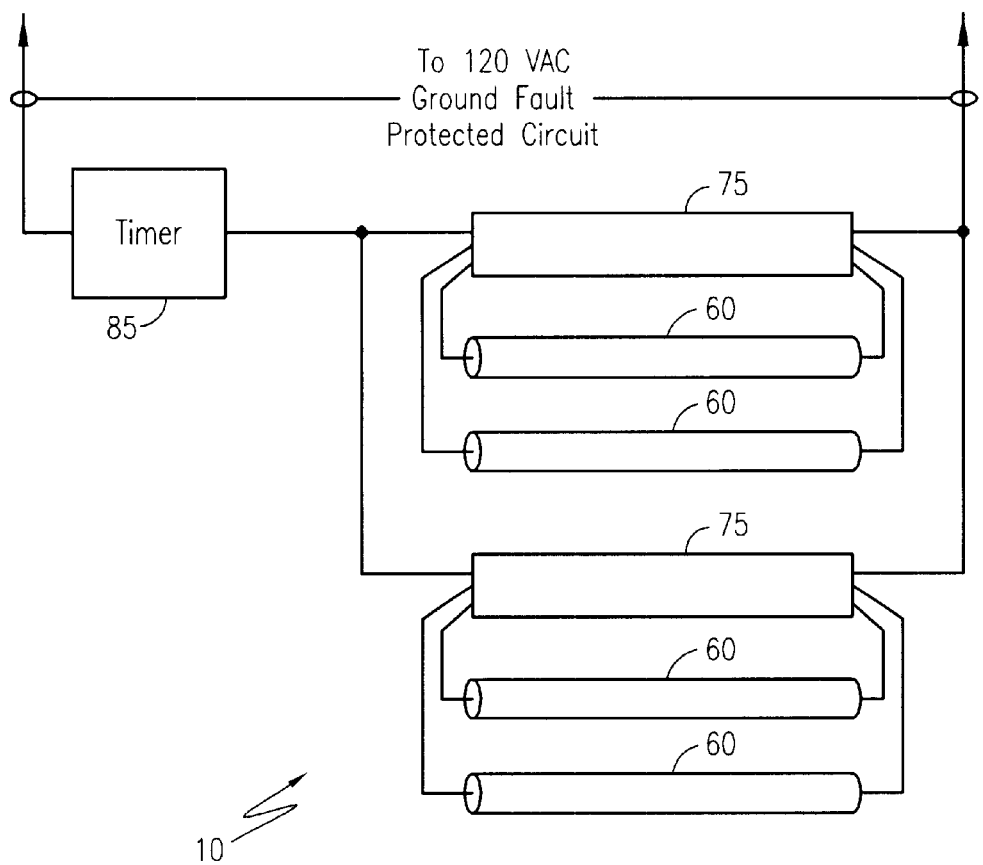
FIG. 4 is an electrical schematic of the shower stall with integral tanning lights 10.

Referring finally to FIG. 4, an electrical schematic of the shower stall with integral tanning lights 10 is shown. Electrical power for the shower stall with integral tanning lights 10 would be derived from a conventional 120 volt alternating current source, commonly found in residential and commercial power systems. For enhanced safety, the power source would be protected by a Ground Fault Circuit Interrupter which would disconnect electrical power in those instances where a current imbalance exists before possible user electrocution can occur. Power from the source is routed through the timer and control mechanism 85 which allows control of the shower stall with integral tanning lights 10. Switched power from the timer and control mechanism 85 is routed to both ballast 75 in a parallel circuit arrangement as shown. Each individual ballast 75 then routes power of the correct current and voltage to each fluorescent tanning tubes 60 as shown. While the arrangement shown indicates two fluorescent tanning tubes 60 per each ballast 75, other combinations such as three or four fluorescent tanning tubes 60 per each ballast 75, which are well known in the art, could also be utilized, and as such should not be a limiting factor of the present invention. A return power path from the opposite side of each ballast 75 is provided to the neutral connection of the 120 volt alternating current power source.

2. Operation of the Preferred Embodiment

The present invention is designed with ease of operation features in mind that allow it to be installed and utilized by a common individual with little or no training. To install the present invention, the user would follow common construction methods used in the installation of conventional shower stalls. Before installation, it must be ensured that adequate wall studs 55 are in place to suit the spacing of the side mounted tanning light 20 and rear mounted tanning light 30. Such construction methods primarily dictate use of the shower stall with integral tanning lights 10 to new construction projects or major bathroom remodeling projects. An adequate source of electrical power must also be provided. After the shower stall itself is installed and connected to suitable water supply and drain connections using conventional plumbing techniques, the user is ready to begin installation of the side mounted tanning light 20, the rear mounted tanning light 30 and the timer and control mechanism 85 into the correct cavities. Internal wiring must first be connected as shown in FIG. 4 using standard wiring techniques, with careful consideration paid to correct grounding methods. Finally the waterproof covers consisting of the tempered glass 120, the frame assembly 110, and the waterproof gasket 105, is put into place and secured using a series of fastening means 115 around the perimeter of the frame assembly 110. At this point the shower stall with integral tanning lights 10 is ready for use.

To use the shower stall with integral tanning lights 10, the user would disrobe and enter the shower stall with integral tanning lights 10 in a manner typical to that of a conventional shower. Next, a suitable operating time is selected on the timer and control mechanism 85, up to a maximum of fifteen minutes. With the fluorescent tanning tubes 60 illuminated, the user simply rotates themselves periodically to obtain an even tan. After the tanning session is complete, the user may take a shower without leaving the shower stall with integral tanning lights 10. It is also envisioned that the user may use the side mounted tanning light 20 and the rear mounted tanning light 30 while concurrently taking a shower as well. Periodic use of the shower stall with integral tanning lights 10 ensures a deep, golden tan year round. If maintenance or replacement of the fluorescent tanning tubes 60 is required, the user can access the interior of the side mounted tanning light 20 and the rear mounted tanning light 30 by removing the fastening means 115 and associated waterproof gasket 105, frame assembly 110 and tempered glass 120.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A shower stall comprising:

a frame;

a front wall affixed to said frame;

a rear wall affixed to said frame opposite said front wall;

a side wall affixed to said frame perpendicular to said front wall and said rear wall;

a shower head mounted on said front wall; and a tanning light provided on said rear wall.

2. The shower stall with integral tanning lights of claim 1, wherein said side mounted tanning light and said rear mounted tanning light are within a cavity formed within said side wall and said rear wall, respectively.

3. The shower stall of claim 2, wherein each of said pair of tanning lights further comprises a pair of fluorescent tanning tubes located on the interior of said side mounted tanning light, each of said pair of fluorescent tanning tubes electrically coupled in a parallel series with a ballast, said ballast routing correct electrical power to said pair of fluorescent tanning tubes.

4. The shower stall of claim 3, wherein each of said pair of tanning lights further comprises a parabolic reflector surrounding each pair of fluorescent tanning tubes for refocusing rearward light rays from said fluorescent tanning tubes to a shower stall interior.

5. The shower stall with integral tanning lights of claim 1, further comprising a timer and control mechanism in electronic control and communication with said pair of tanning lights.

6. The shower stall with integral tanning lights of claim 1, further comprising a top mounted tanning light integrally mounted into a top wall.

7. The shower stall with integral tanning lights of claim 1, further comprising a door section.

* * * * *

UNITED STATES PATENT AND TRADEMARK OFFICE
CERTIFICATE OF CORRECTION

PATENT NO. : 6,567,999 B1
DATED : May 27, 2003
INVENTOR(S) : Keith L. Thurner

It is certified that error appears in the above-identified patent and that said Letters Patent is hereby corrected as shown below:

<u>Column 5, line 23 through Column 6, line 2,</u>
Please correct the Claims as follows:
1.    A shower stall comprising:
    a frame;
    a front wall affixed to said frame;
    a rear wall affixed to said frame opposite said front wall;
    a side wall affixed to said frame perpendicular to said front wall and said rear wall;
    a shower head mounted on said front wall; and
    a floor perpendicularly depending from said front wall, said rear wall and said side wall, said floor comprising an angled surface and a drain;
    a pair of tanning light lights comprising a rear mounted tanning light and a side mounted tanning light, wherein said rear mounted tanning light is provided integrally mounted on said rear wall and said side mounted tanning light is integrally mounted on said side wall;
    a pair of frame assemblies comprising a first frame assembly and a second frame assembly, wherein each of said pair of frame assemblies have a quadrangular perimeter and house a uniform pane of tempered glass, said first frame assembly affixed to said rear wall, and said second frame assembly affixed to said side wall; and
    a pair of waterproof gaskets comprising a first gasket and a second gaskets, said first gasket intermediate to said first tanning light and said first frame assembly, said second gasket intermediate to said second tanning light and said second frame assembly, said pair of waterproof gaskets providing a watertight seal about said pair of tanning lights.

Signed and Sealed this

Ninth Day of August, 2005

JON W. DUDAS
*Director of the United States Patent and Trademark Office*